US006723122B2

(12) United States Patent
Yang et al.

(10) Patent No.: US 6,723,122 B2
(45) Date of Patent: Apr. 20, 2004

(54) CONTAINER AND METHOD FOR STORING AND DELIVERING MINIMALLY-INVASIVE HEART VALVES

(75) Inventors: Jibin Yang, Aliso Viejo, CA (US); Matthew Lane Pease, Mountain View, CA (US); Brandon G. Walsh, Livermore, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 232 days.

(21) Appl. No.: 09/945,392

(22) Filed: Aug. 30, 2001

(65) Prior Publication Data

US 2003/0045928 A1 Mar. 6, 2003

(51) Int. Cl.$^7$ .................................................. A61F 2/24
(52) U.S. Cl. ...................... 623/2.1; 623/2.11; 623/1.12; 206/397; 206/438
(58) Field of Search ................................ 206/438, 397, 206/408; 623/1.11, 1.12, 1.23, 1.24, 1.26, 2.1, 2.11, 2.13, 2.14; 606/108

(56) References Cited

U.S. PATENT DOCUMENTS

| 345,910 A | | 7/1886 | Lloyd | |
|---|---|---|---|---|
| 4,512,471 A | * | 4/1985 | Kaster et al. | 206/438 |
| 5,078,726 A | | 1/1992 | Kreamer | |
| 5,411,552 A | | 5/1995 | Andersen et al. | |
| 5,476,505 A | * | 12/1995 | Limon | 623/1.11 |
| 5,480,424 A | | 1/1996 | Cox | |
| 5,713,949 A | * | 2/1998 | Jayaraman | 623/1.12 |
| 5,960,956 A | | 10/1999 | Langanki et al. | |
| 5,980,570 A | | 11/1999 | Simpson | |
| 5,984,959 A | | 11/1999 | Robertson et al. | |
| 6,027,516 A | * | 2/2000 | Kolobow et al. | 623/1.11 |
| 6,048,360 A | * | 4/2000 | Khosravi et al. | 623/1.11 |

FOREIGN PATENT DOCUMENTS

| WO | WO 99/33414 | 7/1999 |
|---|---|---|
| WO | WO 00/47139 | 8/2000 |

* cited by examiner

*Primary Examiner*—Paul B. Prebilic (57) ABSTRACT

Storage containers for expandable heart valves for minimally invasive valve replacement surgeries are disclosed. The containers permit an expandable valve to be stored in its expanded configuration and then converted to its contracted configuration while still in the container. A mechanism incorporated into the container facilitates the conversion. For example, the container may have a base and a lid, and a crank manipulable from outside. The lid actuates a key within the container that engages the valve to perform the contraction. If the valve is a spirally wound type of expandable valve, the key may be attached to an inner side edge and rotated to wind the valve into a tight spiral. A drain in the container may facilitate removal of a preservative solution so that the valve can be seen during the contraction process, or so that the valve can be rinsed while still within the container.

26 Claims, 9 Drawing Sheets

CONTAINER AND METHOD FOR STORING AND DELIVERING MINIMALLY-INVASIVE HEART VALVES

FIELD OF THE INVENTION

The present invention relates generally to medical devices and particularly to containers and methods for storing and delivering expandable heart valve prostheses especially for use in minimally-invasive surgeries.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves.

Where replacement of a heart valve is indicated, the dysfunctional valve is typically cut out and replaced with either a mechanical valve or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Recently, a great amount of research has been done to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still typically requires bypass, but the excision of the native valve and implantation of the prosthetic valve are accomplished via elongated tubes (catheters or cannulas), with the help of endoscopes and other such visualization techniques. Some examples of recent MIS heart valves are shown in U.S. Pat. No. 5,411,552 to Anderson, et al., U.S. Pat. No. 5,980,570 to Simpson, U.S. Pat. No. 5,984,959 to Robertson, et al., PCT Publication No. 00/047139 to Garrison, et al., and PCT Publication No. WO 99/334142 to Vesely.

To minimize the possibility of damage to the relatively delicate tissue type or bioprosthetic heart valves, they are packaged in jars filled with preserving solution for shipping and storage prior to use in the operating theater. In doing so, the valves are stabilized to prevent the valves from striking the inside of the jar. Prior to implantation in a patient, residual traces of the preserving solution need to be washed from the valve. This washing is accomplished by first removing the valve from the jar and then rinsing the valve in a shower. Alternatively, the valve may be immersed and agitated in a bath. Typically, the medical technician removes the valve from its jar by grasping a valve holder with a gloved hand. The valve holder is typically centrally located with respect to, and sutured to, the valve sewing ring. A surgical handle is then threaded into a socket provided in the valve holder. The valve is then rinsed in the bath or shower while being held at the end of the handle. After rinsing, the handle is used to position the valve in the appropriate implantation site. This conventional process leaves the valve susceptible to damage if the valve strikes a surface while being manipulated on the end of the surgical handle.

Despite some advances in minimally-invasive valve design, there remains a need for a storage and delivery system for such valves that prevents damage to the biological valve, and enables a medical practitioner to easily and safely prepare, remove and rinse the valve.

SUMMARY OF THE INVENTION

The present invention provides a storage container for an expandable prosthetic heart valve having both contracted and expanded configurations. In one embodiment, the storage container is sized to receive the heart valve in its expanded configuration, and a mechanism incorporated into the container engages the heart valve and operates to convert the heart valve from its expanded to its contracted configuration. The heart valve may be a tissue-type valve having flexible leaflets and the container holds a solution suitable for preserving the leaflets. The container desirably includes a base and a lid, and the mechanism operable to convert the heart valve from its expanded to its contracted configuration may be partially incorporated into the lid. The base may have a drain to empty the solution from the container. In a preferred embodiment, the mechanism operable to convert the heart valve from its expanded to its contracted configuration is separable from the base such that the heart valve in its contracted configuration may be removed from the base by manipulating the lid.

The heart valve may comprise a generally sheet-like stent body that is spirally-wound about an axis in the contracted configuration and is substantially unwound and at least partly forms a tube centered about the axis in its expanded configuration. The stent body defines a pair of opposed side edges that generally mate in the expanded configuration, and the mechanism includes a key attached to a first side edge, wherein the key rotates to wind the valve from its expanded to its contracted configuration. The mechanism further may include a clamp releasably attached to the container and to a second side edge of the heart valve opposite the first side edge such that the second side edge is held stationary with respect to the container while the key attached to the first side edge rotates. The container desirably includes a base and a lid, wherein the key rotatably couples to the lid and the clamp releasably attaches to the base. The key desirably comprises a shaft passing through the lid and has structure for engaging complementary structure on the first side edge of the heart valve, wherein the storage container further includes a crank rotatably affixed to the shaft and operable from the exterior side of the lid. The clamp preferably comprises a dovetail slide and the base includes a complementary channel for receiving the slide, the dovetail slide further including structure for engaging complementary structure on the second side edge of the heart valve.

In a further aspect, the invention provides a system for storing and delivering an expandable prosthetic heart valve having both contracted and expanded configurations. The system includes a prosthetic heart valve having a generally sheet-like stent body that is spirally-wound about an axis in the contracted configuration and is substantially unwound and at least partly forms a tube centered about the axis in its expanded configuration, the stent body defining a pair of opposed side edges that generally mate in the expanded configuration. In addition, a plurality of flexible, biocompatible membranes incorporated into the stent body form the heart valve leaflets in the second configuration. The system includes a container sized to receive the heart valve in its expanded configuration. A mechanism incorporated into the container winds the heart valve within the container. Preferably, the heart valve is a tissue-type valve and the container holds a solution suitable for preserving the leaflets. Also, the container may include a base and a lid, and the mechanism incorporated into the container for winding the heart valve within the container is partially incorporated into the lid. The base may have a drain to empty the solution from the container.

In a further aspect of the present invention, a method of storing and delivering an expandable prosthetic heart valve having both contracted and expanded configurations is provided. The method comprises providing a prosthetic heart valve having a contracted configuration sized to be delivered to a site of implantation through a catheter and an expanded configuration sized to engage a heart valve annulus. The method further includes storing the heart valve in a container in its expanded configuration, and converting the heart valve from its expanded to its contracted configuration while in the container. Where the heart valve is a rolled-type of valve, the step of converting comprises winding the valve from a relatively large spiral to a relatively tight spiral. The container may include a base and a lid, and a crank rotatably connected to an inner side edge of the valve, and the step of winding comprises turning the crank to wind the inner side edge of the valve. The step of storing preferably includes providing a solution within the container and the method includes draining the solution from the container while the valve remains within the container. The method may further include rinsing the valve after draining the solution from the container and while the valve remains within the container.

A further understanding of the nature and advantages of the invention will become apparent by reference to the remaining portions of the specification and drawings.

DESCRIPTION OF THE PREFERRED EMBODIMENTS

The present invention provides a storage container for a minimally invasive prosthetic heart valve that also facilitates delivery and implantation of the valve. Minimally invasive heart valves come in a variety of designs, including directly radially expandable types and so-called "rolled" heart valves that are spirally wound into a contracted configuration and expanded by unwinding. The presently illustrated heart valve is of the latter type, but it should be understood that the principles of the present invention are applicable to all types of expandable heart valves.

In essence, the present invention provides a single vehicle for storing, preparing, and handling an expandable prosthetic heart valve just prior to implantation. Many minimally invasive heart valves include flexible leaflets typically made from bioprosthetic animal tissue. The embodiment illustrated herein is a more recently developed variation which discloses a rolled-type prosthetic heart valve using bovine pericardial leaflets. This valve is similar to that shown and described in co-pending U.S. patent application Ser. No. 09/815,521, expressly incorporated herein by reference. Whatever the material of the flexible leaflets, it is advantageous to store them in a relaxed state to minimize folding or compression of the leaflets. However, to deliver such expandable heart valves, they must be contracted to pass through a relatively small diameter delivery tube, thus requiring folding and compressing of the leaflets. The present invention enables the storage of a heart valve in its expanded configuration to better protect the flexible leaflets during the potentially long storage times, and permit easy contraction of the heart valve just prior to delivery.

It should be understood, therefore, that a number of aspects of the present invention are applicable to all types of expandable heart valves. That is, various mechanisms for contracting heart valves within a storage container are anticipated by the disclosure herein, and thus the invention should not be limited to the illustrated embodiment. For example, mechanisms currently known for contracting expandable stents around balloons could be incorporated into the storage container of the present invention to adapt to those expandable heart valves that more closely resemble conventional stents (i.e., those that do not unroll but are directly radially expanded using an internal balloon or expansion device, wherein the expanded shape is maintained by inherent elastic and/or plastic material properties).

With these principles in mind, the invention will now be described in detail with respect to the attached drawings.

Figure 1:
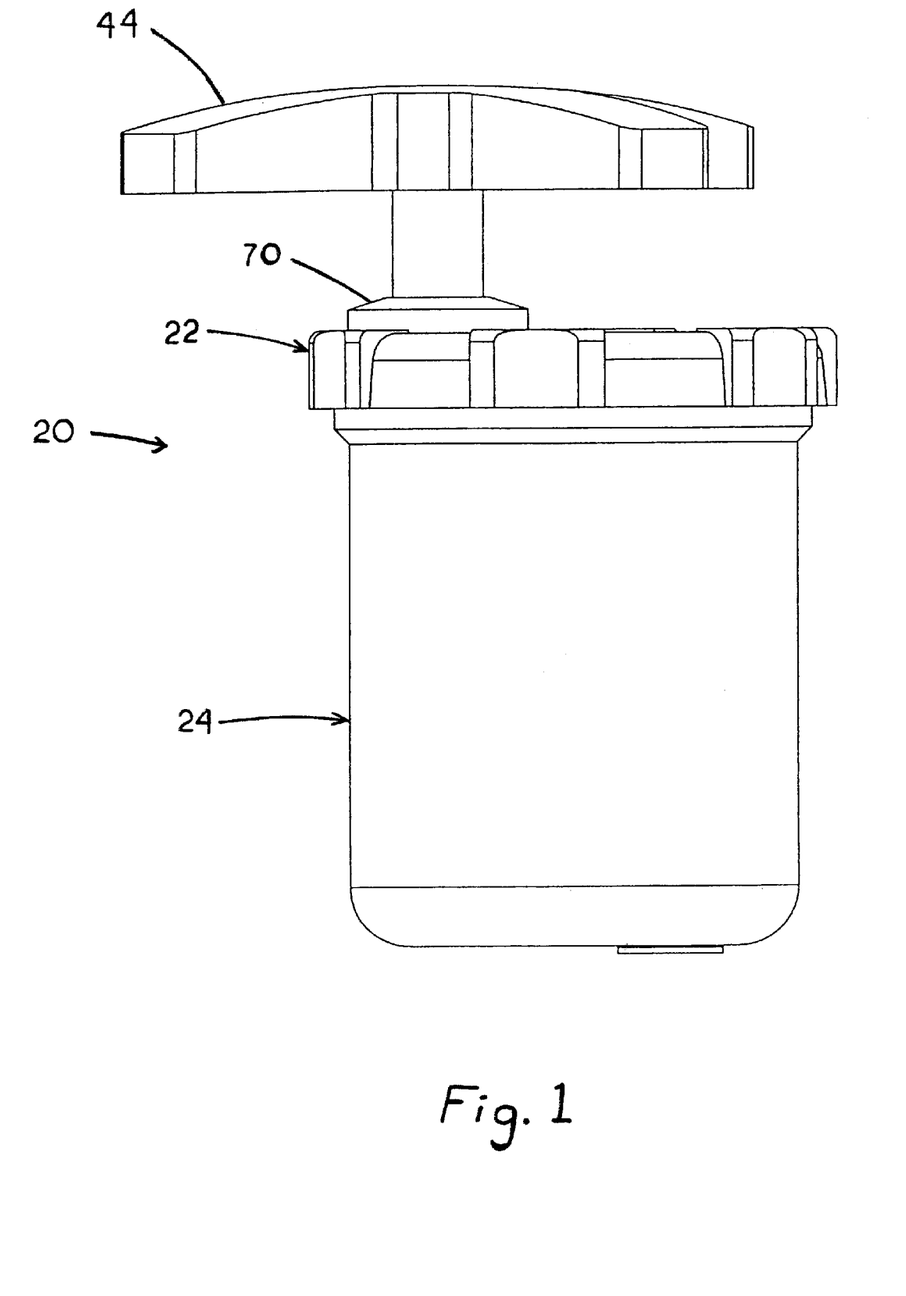
FIG. 1 is an elevational view of a prosthetic heart valve storage container of the present invention.

FIG. 1 illustrates in elevational view an assembled storage container 20 of the present invention generally comprising a lid 22 covering the open mouth of a base 24. As shown, the base 24 is generally cylindrical in exterior shape, and the lid is disk-shaped having a conventional flange overlapping the open mouth of the base. Although not shown, the lid 22 desirably couples to the base 24 using appropriate threading or snap-on features. The storage container 20 is typically useful for storing bioprosthetic heart valves having leaflets that require wet storage, typically in a preservative. Therefore, when the lid 22 is coupled to the base 24, the container 20 is desirably leak-proof. The components of the storage container may be made of a variety of corrosion-resistant materials, though molded polymers are preferred.

Figures 2, 2A:
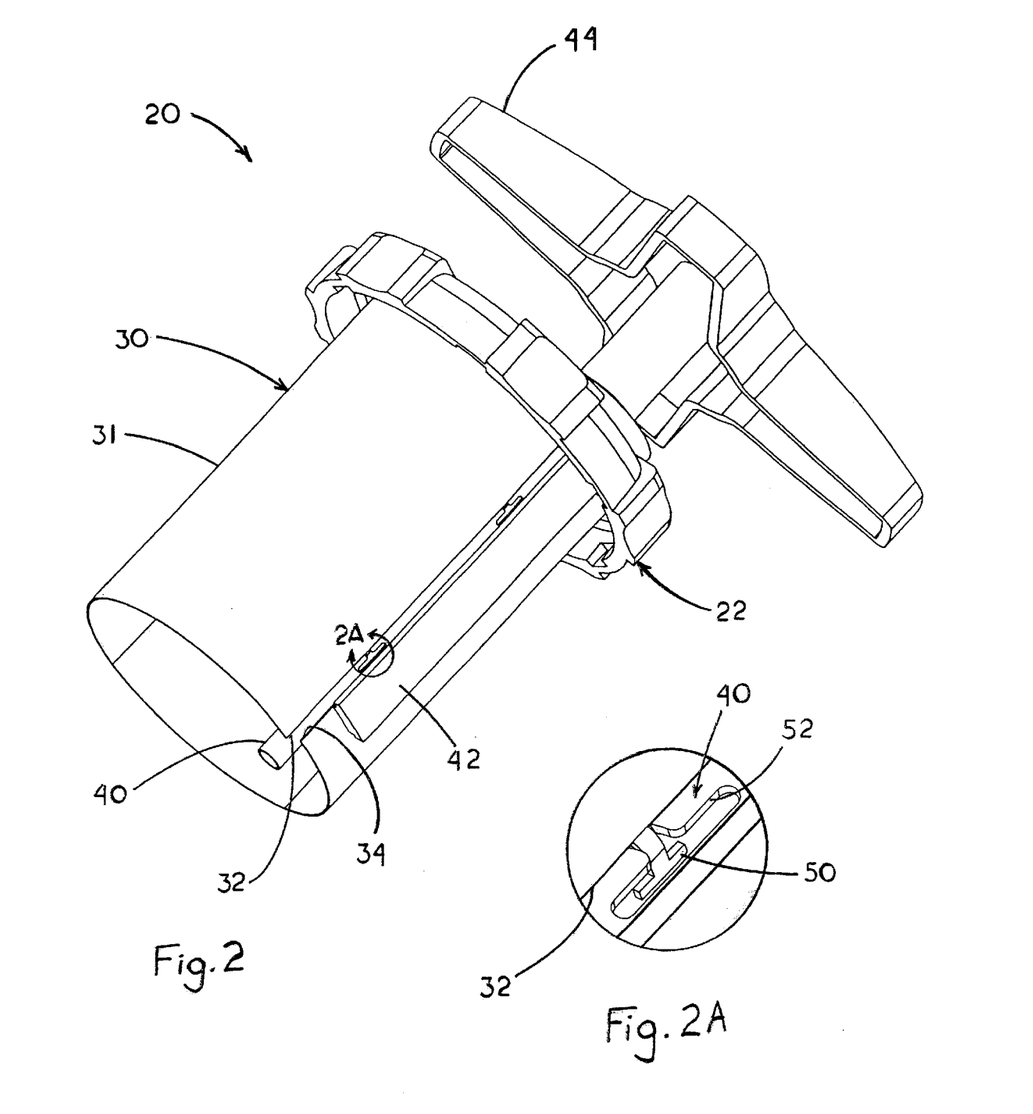
FIG. 2 is a perspective exploded view of the heart valve storage container of FIG. 1 with a base portion removed and showing the valve in its unrolled or expanded configuration.
FIG. 2A is a detailed view of the cooperating engagement between a rolled prosthetic heart valve and a winding key taken within circle 2A of FIG. 2.

FIG. 2 illustrates the storage container 20 with the base 24 removed, and schematically shows a rolled-type prosthetic heart valve 30 coupled to the lid 22. The heart valve 30 may be formed of the generally rectangular sheet-like stent body 31 having a first side edge 32 and a second side edge 34. When expanded, the first side edge 32 desirably mates with the second side edge 34 to form a tubular structure suitable for mounting in the native valve annulus. Flexible or bioprosthetic leaflets mounted in windows in the sheet-like stent body 31 are not illustrated for clarity, though various embodiments are disclosed in co-pending U.S. patent application Ser. No. 09/815,521.

A mechanism for converting the prosthetic heart valve 30 from its illustrated expanded configuration to a rolled or spirally-wound contracted configuration includes a key 40 that engages the first side edge 32, a clamp 42 that engages the second side edge 34, and a crank handle 44 rotatably coupled to the key 40 through the lid 22.

Figures 3, 4:
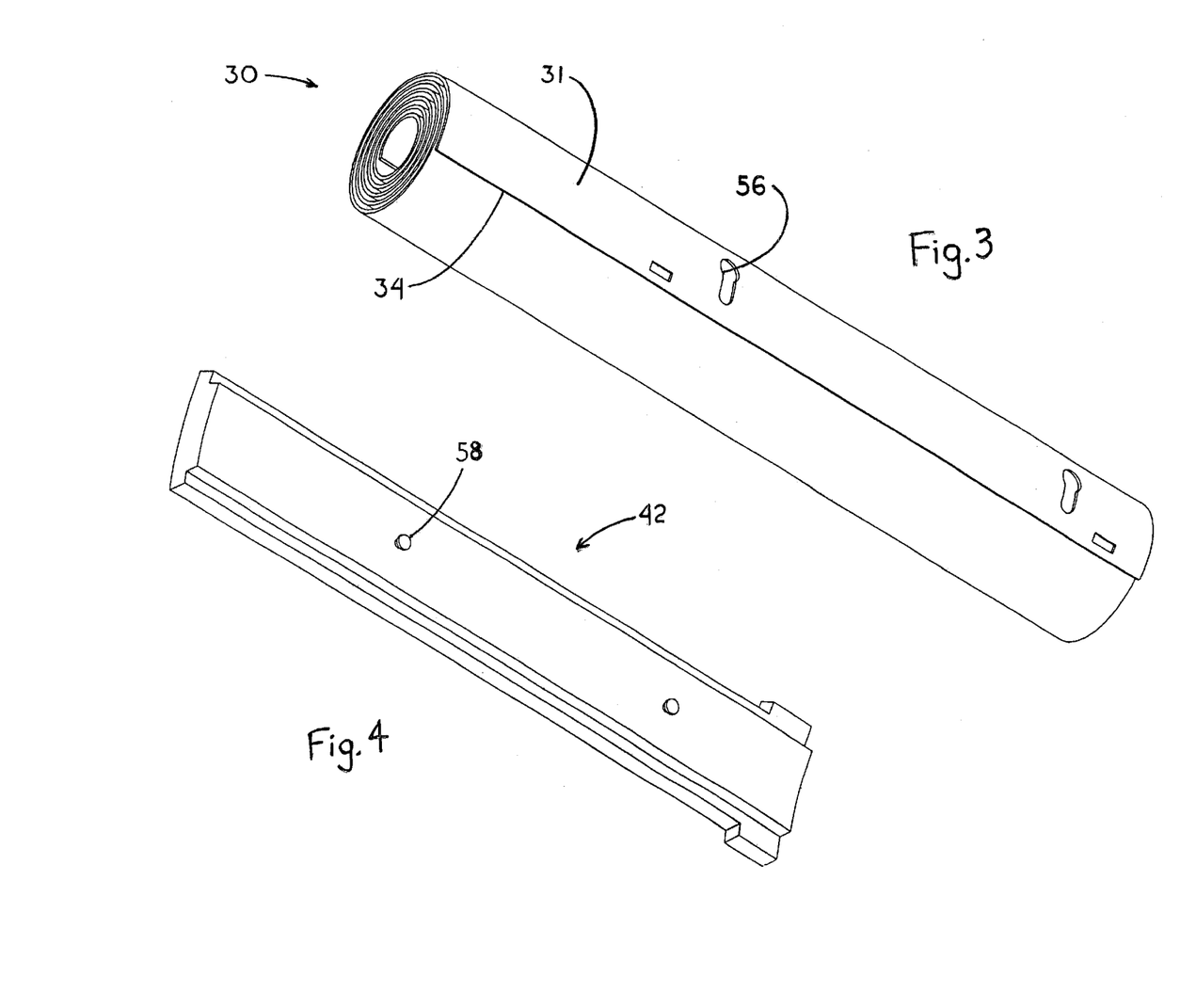
FIG. 3 is a perspective view of the rolled or contracted prosthetic heart valve in isolation.
FIG. 4 is a perspective view of a clamp that attaches to a second side edge of the rolled heart valve using tabs.
Figure 5:
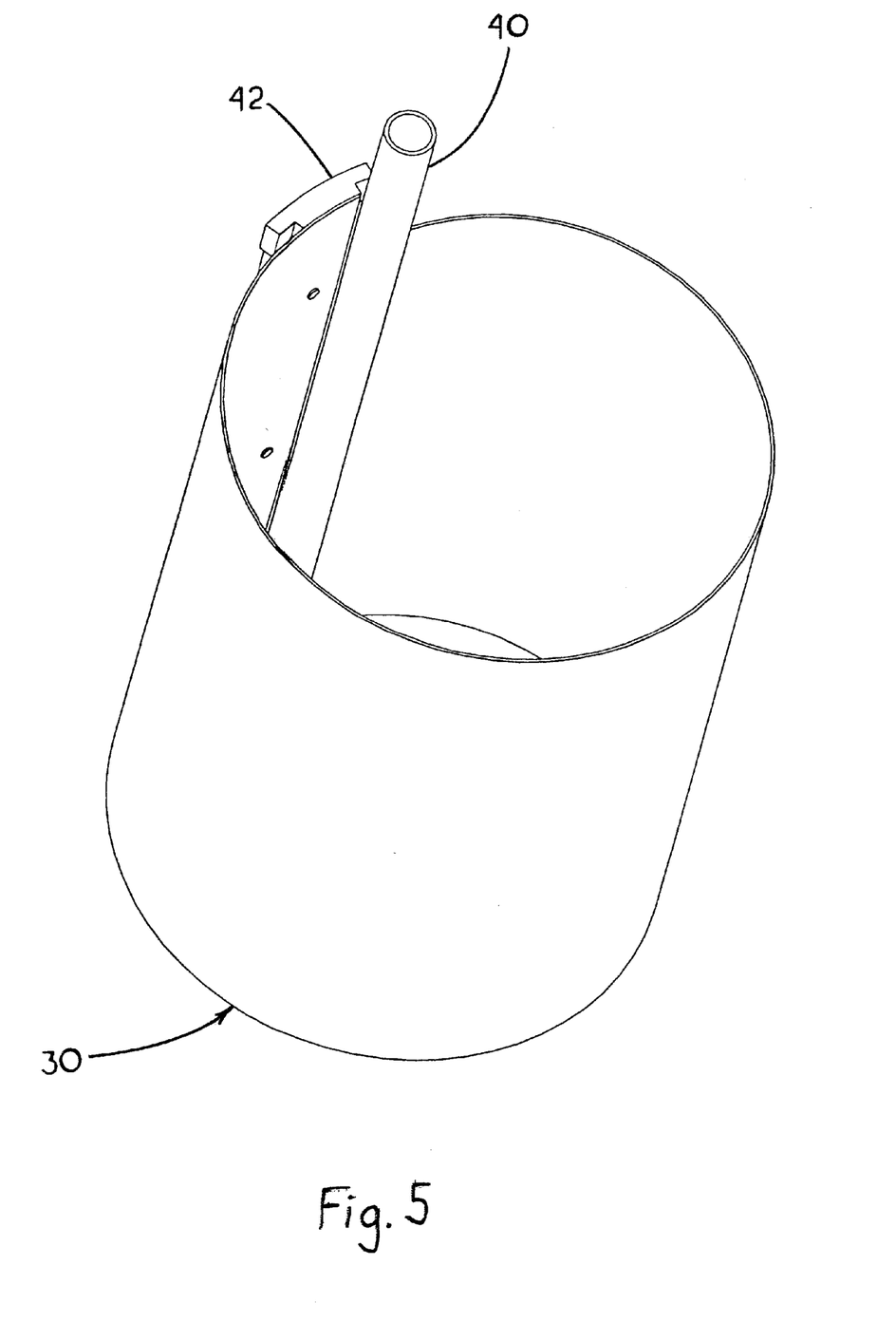
FIG. 5 is a perspective view of the unrolled prosthetic heart valve and a mechanism for winding the valve including the key attached to one side edge, and the clamp attached to the second side edge.

Various means are contemplated for releasably attaching the key 40 to the first side edge 32, and the clamp 42 to the second side edge 34. For example, as seen in the detailed view of FIG. 2A the first side edge 32 may include a plurality of T-shaped tabs 50 bent from the adjacent stent body 31 so as to engage complementary T-shaped slots 52 provided in the key 40. In the illustrated embodiment, the key 40 is a hollow tube that accommodates the tabs 50. Likewise, FIG. 3 illustrates the heart valve 30 in a rolled up or contracted configuration and shows a plurality of keyhole-shaped cutouts 56 adjacent the second side edge 34 of the stent body 31 that mate with buttons 58 provided in the clamp 42 (see FIG. 4). Each button 58 includes a narrowed neck portion and an enlarged head portion that fits through the enlarged opening in one of the cutouts 56, the button then being displaced such that the neck portion resides within the narrow opening of the cut out. The directionality of the means for releasably attaching the heart valve 30 to the key 40 and clamp 42 is such that the valve can be converted from its expanded configuration as seen in FIGS. 2 and 5, to its contracted configuration, at which time the valve can be detached from the key and clamp for subsequent implantation.

Figure 6:
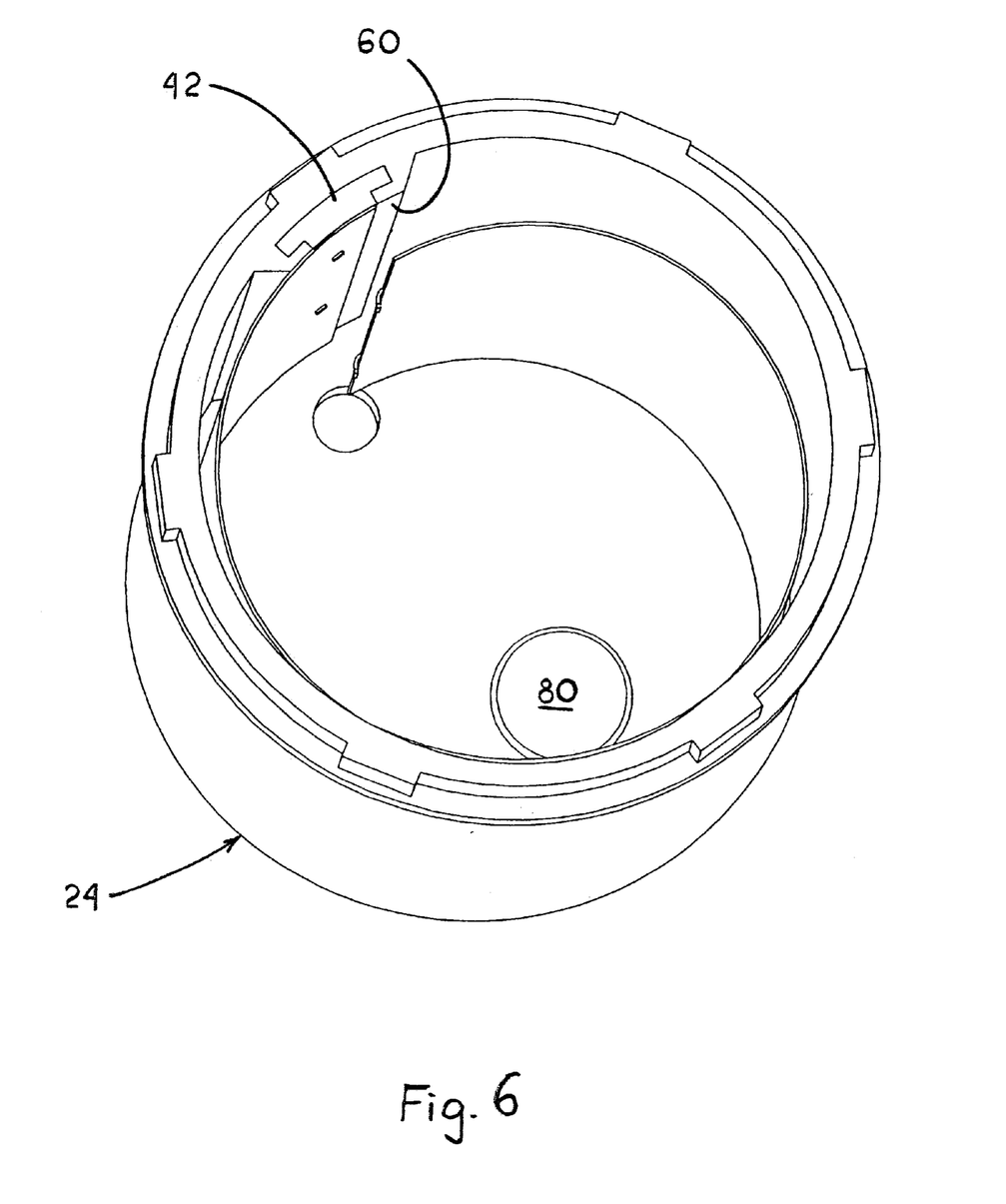
FIG. 6 is a perspective view looking into the base portion of the storage container of the present invention and showing the unrolled prosthetic heart valve therewithin attached to a dovetail-type clamp.
Figure 7A:
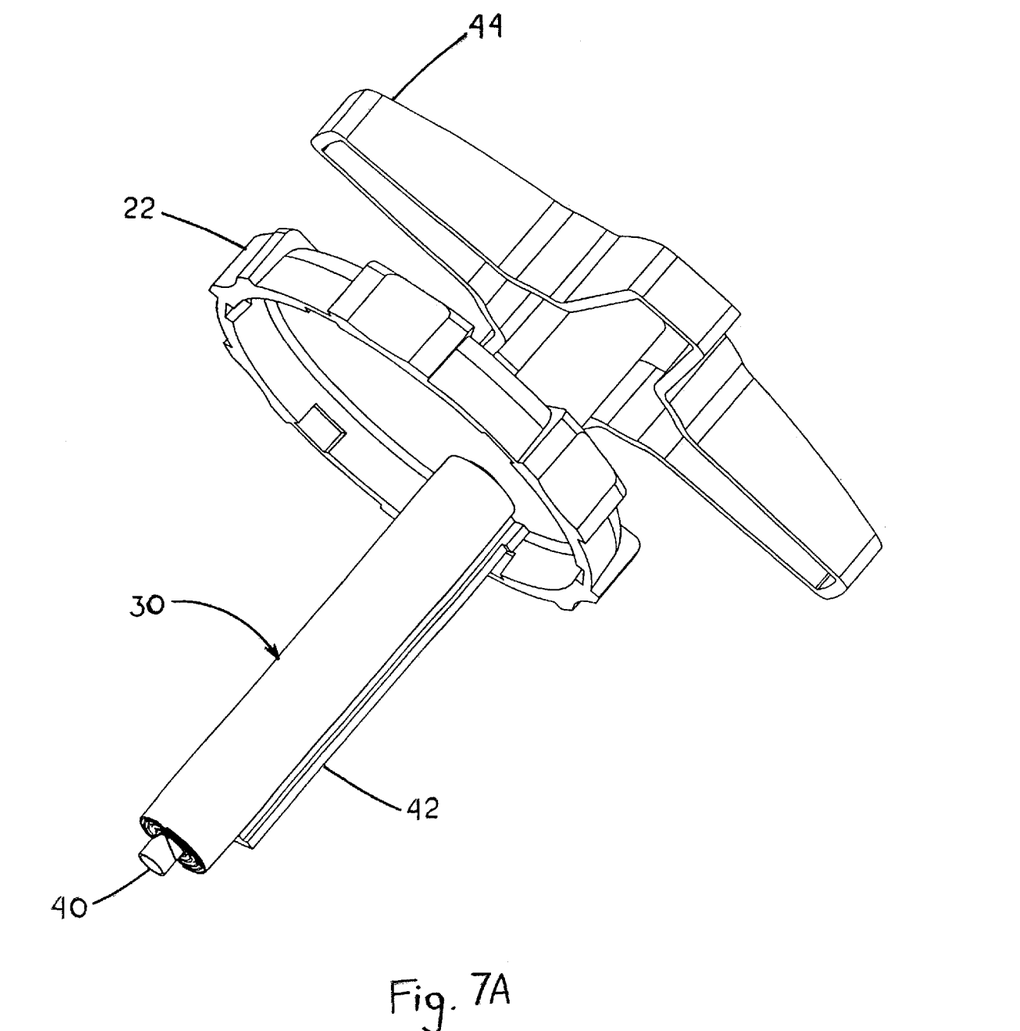
FIG. 7A is a perspective view of a lid portion of the storage container showing a prosthetic heart valve attached thereto in its contracted configuration.
Figure 7B:
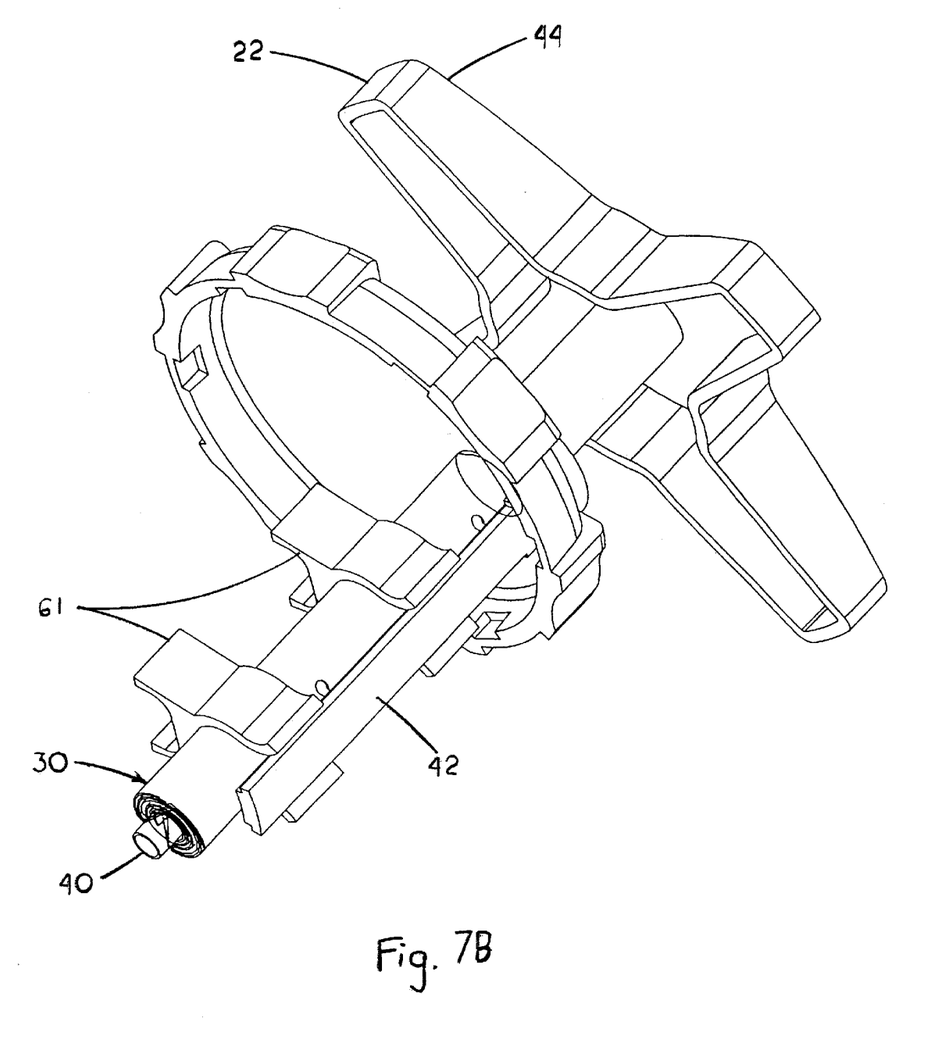
FIG. 7B is a perspective view as in FIG. 7A of the heart valve attached to the lid portion of the storage container and maintained in its contracted configuration by a pair of clips.

The conversion of the heart valve 30 from its expanded to its contracted configuration will now be described. The key 40 and clamp 42 work in conjunction to relatively circumferentially displace the first side edge 32 with respect to the second side edge 34. In the exemplary embodiment, the clamp 42 (and second side edge 34) releasably attaches to an inner wall of the base 24 while the key 40 (and first side edge 32) rotates along a fixed axis within the base 24. After the heart valve 30 has been converted to its contracted configuration, it may be removed along with the key 40 and clamp 42 from the base 24. In this regard, the clamp 42 comprises an elongated member having the characteristics of a dovetail slide so as to fit within a cooperating channel in the inner wall of the base 24 formed by a pair of inwardly directed flanges 60, as seen in FIG. 6. After the heart valve 30 has been rolled or wound up into its contracted configuration, it may be linearly removed along with the clamp 42 from the base 24, as best seen in FIG. 7A. One or more clips 61 as seen in FIG. 7B may be added to surround the heart valve 30 and temporarily constrain it in its rolled configuration. The heart valve 30 may then be disconnected from the storage container components, including the winding key 40.

Figure 8A:
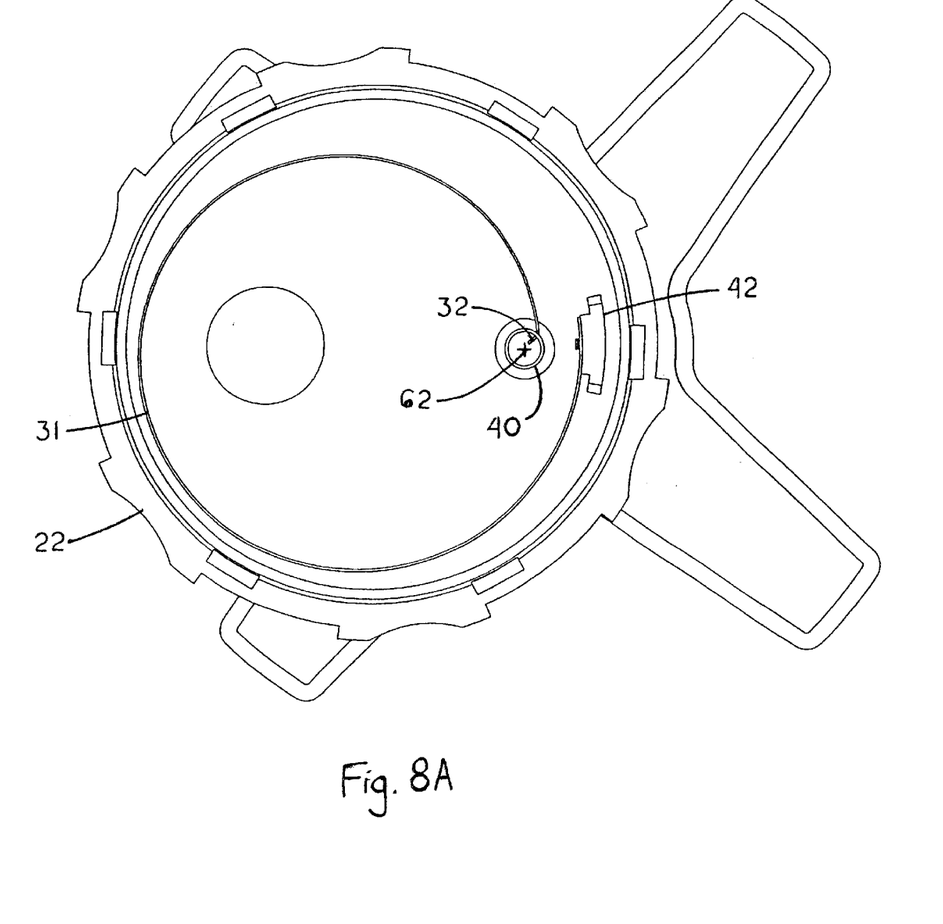
FIG. 8A is a horizontal sectional view taken through the base portion of the storage container and showing the prosthetic heart valve therewithin in its expanded configuration.
Figure 8B:
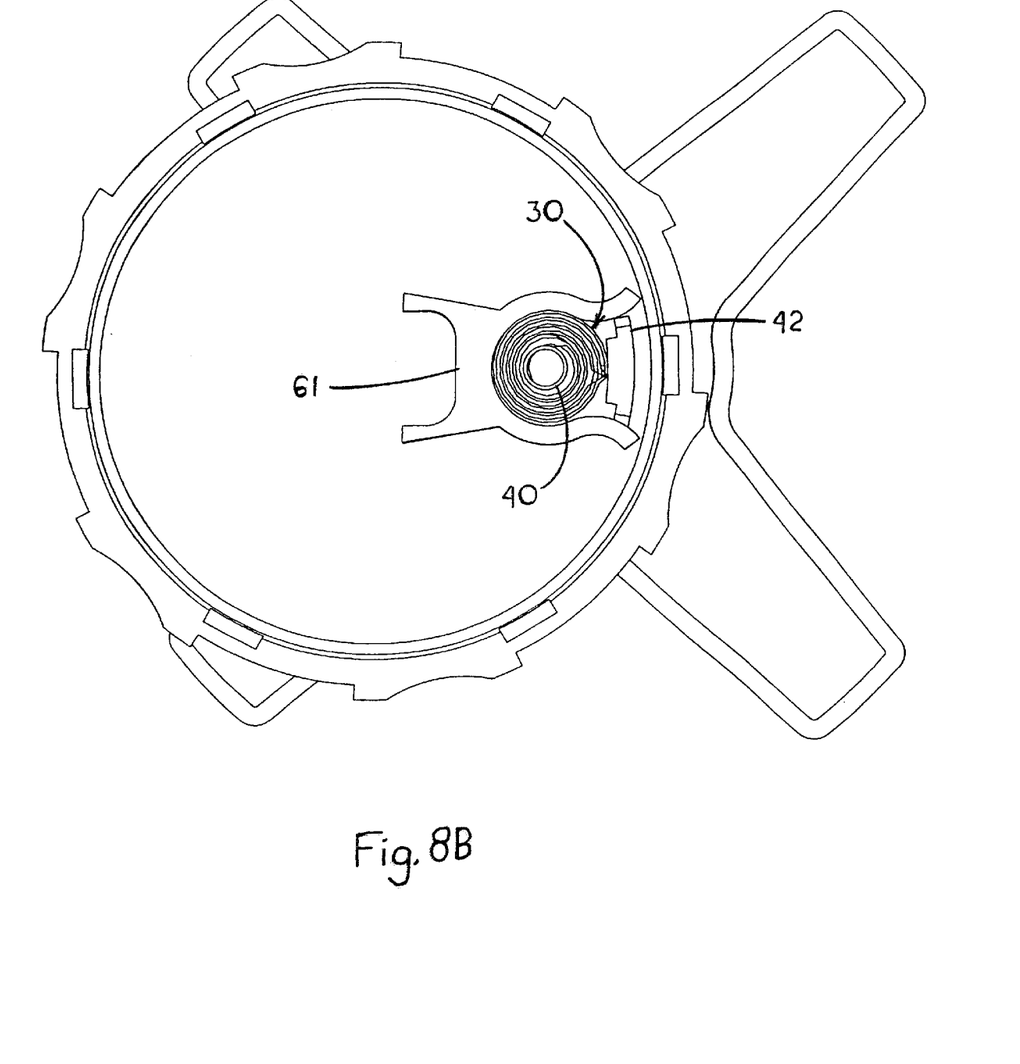
FIG. 8B is a horizontal sectional view taken through the base portion of the storage container and showing the prosthetic heart valve therewithin maintained in its contracted configuration with clips.

The winding operation that converts the heart valve 30 from its expanded configuration to its contracted configuration is seen in two stages in FIGS. 8A and 8B. In FIG. 8A, the sheet-like stent body 31 of the valve 30 is seen defining a relatively large spiral closely fitting within the base 24. The key 40 is shown attached to the first side edge 32 and positioned just radially inward in the container with respect to the clamp 42 to which the second side edge 34 is attached. As will be described in greater detail below, the key 40 rotates about an axis 62 fixed within the container. From the perspective of FIG. 8A, rotating the key 40 about the axis 62 in a clockwise direction winds the sheet-like stent body 31 into a relatively tight spiral, as seen in FIG. 8B. The thickness of the stent body 31 and number of windings of the body in the contracted configuration determines the spacing between the key 40 and clamp 42. Desirably, the spacing is as shown such that the contracted configuration of the valve 30 fills the space between the key 40 and clamp 42. FIG. 8B also shows the clip 61 constraining the heart valve 30 in its contracted configuration.

With reference to FIGS. 1, 2, and 7, the key 40 comprises a shaft journaled through the lid 22 and turned by the crank 44. In a preferred embodiment, a ratchet device (not shown) is provided within a hub 70 (FIG. 1) contained within the lid 22 to prevent reverse rotation of the key 40. After the heart valve 30 has been wound up, it may be removed from the base 24 along with the assembly of the lid 22, key 40, and crank 44, as seen in FIG. 7A. Subsequently, the contracted valve 30 is constrained from re-expansion by clips (such as the clips 61 seen in FIG. 7B), bands, sutures, or other similar expedient to prevent premature expansion prior to delivery to an implantation site. For example, features on the second side edge 34 may engage cooperating features in the sheet-like stent body 31 to lock the stent in its spirally wound configuration. These features can then be released when expansion of the stent body is desired.

As mentioned above, a preferred expandable heart valve includes the stent body 31 and a plurality of flexible leaflets (not shown). If the leaflets need to remain hydrated during storage, such as if they are made of bioprosthetic material, the entire container 20 may be filled with a preservative solution during storage. To facilitate implantation of the valve 30, the base 24 desirably incorporates a drain, such as the drain hole 80 seen in the bottom wall of the base in FIG. 6. Alternatively, the entire bottom wall of the base 24 may be removable, such as with threading. Just prior to use of the valve 30, the preservative solution is drained from within the base 24. If the entire bottom wall of the base 24 is removed, the valve 30 in its expanded configuration is thus exposed so that the valve can be seen during the contraction process and can be rinsed while in the container in either the contracted or expanded configuration, thus reducing the chance of damage to the valve. Alternatively, the crank 44 is used to convert the valve 30 into its contracted configuration, which is then removed from the base 24 as seen in FIGS. 7A and 7B. The valve 30 in its contracted configuration can then be rinsed.

While the foregoing describes the preferred embodiments of the invention, various alternatives, modifications, and equivalents may be used. Moreover, it will be obvious that certain other modifications may be practiced within the scope of the appended claims.

What is claimed is:

1. A storage container for an expandable prosthetic heart valve having both contracted and expanded configurations, comprising:
    a container sized to receive the heart valve in its expanded configuration;
    a mechanism incorporated into the container and engaging the heart valve operable to convert the heart valve from its expanded configuration to its contracted configuration.

2. The storage container of claim 1, wherein the base has a drain to empty the solution from the container.

3. The storage container of claim 1, wherein the mechanism operable to convert the heart valve from its expanded to its contracted configuration is separable from the base such that the heart valve in its contracted configuration may be removed from the base by manipulating the lid.

4. The storage container of claim 1, wherein the heart valve comprises a generally sheet-like stent body that is spirally-wound about an axis into the contracted configuration and is substantially unwound and at least partly forms a tube centered about the axis in its expanded configuration, the stent body defining a pair of opposed side edges that generally mate in the expanded configuration, wherein the mechanism includes a key attached to a first side edge, and wherein the key rotates to wind the valve from its expanded to its contracted configuration.

5. The storage container of claim 4, wherein the mechanism further includes a clamp releasably attached to the container and to a second side edge of the heart valve opposite the first side edge such that the second side edge is held stationary with respect to the container while the key attached to the first side edge rotates.

6. The storage container of claim 5, wherein the container includes a base and a lid, and wherein the key is rotatably coupled to the lid and the clamp releasably attaches to the base.

7. The storage container of claim 6, wherein the key comprises a shaft passing through the lid and having structure for engaging complementary structure on the first side edge of the heart valve, and the storage container further includes a crank rotatably affixed to the shaft and operable from the exterior side of the lid.

8. The storage container of claim 6, wherein the clamp comprises a dovetail slide and the base includes a complementary channel for receiving the slide, the dovetail slide further including structure for engaging complementary structure on the second side edge of the heart valve.

9. A system for storing and delivering an expandable prosthetic heart valve having both contracted and expanded configurations, comprising:
    a prosthetic heart valve comprising a generally sheet-like stent body that is spirally-wound about an axis in the contracted configuration and is substantially unwound and at least partly forms a tube centered about the axis in its expanded configuration, the stent body defining a pair of opposed side edges that generally mate in the expanded configuration;
    a plurality of flexible, biocompatible membranes incorporated into the stent body to form heart valve leaflets in the expanded configuration;
    a container sized to receive the heart valve in its expanded configuration; and
    a mechanism incorporated into the container for winding the heart valve within the container into its contracted configuration.

10. The system of claim 9, wherein the heart valve is a tissue-type valve and the container holds a solution suitable for preserving the leaflets.

11. The system of claim 10, wherein the container includes a base and a lid, and the mechanism incorporated into the container for winding the heart valve within the container is partially incorporated into the lid.

12. The system of claim 11, wherein the base has a drain to empty the solution from the container.

13. The system of claim 11, wherein the mechanism incorporated into the container for winding the heart valve within the container is separable from the base such that the heart valve in its contracted configuration may be removed from the base by manipulating the lid.

14. The system of claim 9, wherein the mechanism includes a key attached to a first side edge of the stent body, wherein the key rotates to wind the valve from its expanded to its contracted configuration.

15. The system of claim 14, wherein the mechanism further includes a clamp releasably attached to the container and to a second side edge of the stent body opposite the first side edge such that the second side edge is held stationary with respect to the container while the key attached to the first side edge rotates.

16. The system of claim 15, wherein the container includes a base and a lid, and wherein the key is rotatably coupled to the lid and the clamp releasably attaches to the base.

17. The system of claim 16, wherein the key comprises a shaft passing through the lid and having structure for engaging complementary structure on the first side edge of the stent body, and the storage container further includes a crank rotatably affixed to the shaft and operable from the exterior side of the lid.

18. The system of claim 16, wherein the clamp comprises a dovetail slide and the base includes a complementary channel for receiving the slide, the dovetail slide further including structure for engaging complementary structure on the second side edge of the stent body.

19. The system of claim 9, further including a clip for holding the heart valve in its contracted configuration.

20. A method of storing and delivering an expandable prosthetic heart valve having both contracted and expanded configurations, the method comprising:
    providing a prosthetic heart valve having a contracted configuration sized to be delivered to a site of implantation through a tube and an expanded configuration sized to engage a heart valve annulus;
    storing the heart valve in a container in its expanded configuration;
    converting the heart valve from its expanded configuration to its contracted configuration while in the container.

21. The method of claim 20, wherein the heart valve is a rolled-type of valve and the step of converting comprises winding the valve from a relatively large spiral to a relatively tight spiral.

22. The method of claim 21, wherein the container includes a base and a lid, and a crank rotatably connected to an inner side edge of the valve, and the step of winding comprises turning the crank to wind the inner side edge of the valve.

23. The method of claim 20, wherein the step of storing includes providing a solution within the container and the method includes draining the solution from the container while the valve remains within the container.

24. The method of claim 23, further including rinsing the valve after draining the solution from the container and while the valve remains within the container.

25. The method of claim 20, wherein the heart valve is a rolled-type of valve and the step of converting comprises spirally winding the valve and maintaining the valve in its wound state using a constraint around the valve.

26. The method of claim 25, further including detaching the heart valve from the storage container after placing the constraint around the valve and mounting the valve on a delivery catheter.

\* \* \* \* \*